(12) United States Patent
Winslow et al.

(10) Patent No.: US 6,773,613 B1
(45) Date of Patent: Aug. 10, 2004

(54) METHOD FOR PRODUCTION OF STROMA-FREE HEMOGLOBIN

(75) Inventors: Robert M. Winslow, La Jolla, CA (US); Kim D. Vandegriff, San Diego, CA (US)

(73) Assignee: Sangart, Inc., San Diego, CA (US)

( * ) Notice: Subject to any disclaimer, the term of this patent is extended or adjusted under 35 U.S.C. 154(b) by 0 days.

(21) Appl. No.: 09/807,565

(22) PCT Filed: Oct. 15, 1999

(86) PCT No.: PCT/US99/24149
§ 371 (c)(1),
(2), (4) Date: Jul. 20, 2001

(87) PCT Pub. No.: WO00/21591
PCT Pub. Date: Apr. 20, 2000

Related U.S. Application Data

(60) Provisional application No. 60/122,180, filed on Mar. 1, 1999, and provisional application No. 60/104,319, filed on Oct. 15, 1998.

(51) Int. Cl.[7] .................. B01D 21/26; C07K 14/805
(52) U.S. Cl. .................. 210/806; 210/739; 210/749; 210/764; 210/787; 435/2; 436/177; 514/6; 530/385
(58) Field of Search .................. 210/645, 646, 210/650, 651, 739, 749, 782, 787, 764, 806; 424/533; 435/2; 436/177, 178; 514/6; 530/385

(56) References Cited

U.S. PATENT DOCUMENTS

| | | |
|---|---|---|
| 4,303,193 A | 12/1981 | Latham, Jr. |
| 4,401,652 A | 8/1983 | Simmonds et al. |
| 5,296,465 A | 3/1994 | Rausch et al. |
| 5,464,814 A | 11/1995 | Sehgal et al. |
| 5,646,252 A | 7/1997 | Berbers et al. |
| 5,814,601 A | 9/1998 | Winslow et al. |
| 5,921,950 A | 7/1999 | Toavs et al. |

FOREIGN PATENT DOCUMENTS

EP    0 367 475    5/1990

OTHER PUBLICATIONS

Vandegriff and Shrager, Meth. Enzymol. (1994) 232:460–485.
Winslow and Chapman, Meth. Enzymol. (1994) 231:3–16.

Primary Examiner—John Kim
(74) Attorney, Agent, or Firm—Burns Doane Swecker & Mathis LLP

(57) ABSTRACT

The invention relates to a system and a method of using an automated blood cell separator to prepare a high-quality hemoglobin solution as the raw material for manufacture of hemoglobin-based therapeutic oxygen carriers, so-called "blood substitutes". The method of isolating stroma-free hemoglobin comprises the steps of: separating the red blood cells from the starting solution; washing the red blood cells in wash solution; contacting the red blood cells with a hypotonic solution to produce stromata and a hemolysate containing hemoglobin having an ionic strength and separating the hemolysate from the stromata. Further, the invention relates to a method for preparing a chemically modified hemoglobin solution. This method comprises the steps of: separating the red blood cells from the staring solution; washing the red blood cells in wash solution; contacting the red blood cells with a hypotonic solution to produce stromata and a hemolysate containing hemoglobin having an ionic strength; separating the hemolysate from the stromata; and mixing the hemolysate with a reagent adapted to chemically modify the hemoglobin to form a chemically modified hemoglobin solution.

15 Claims, 2 Drawing Sheets

METHOD FOR PRODUCTION OF STROMA-FREE HEMOGLOBIN

RELATED APPLICATIONS

This application claims priority to provisional applications Ser. No. 60/104,319, filed Oct. 15, 1998, and Ser. No. 60/122,180, filed March 1, 1999. The disclosures of the identified provisional applications are incorporated by reference in their entireties.

FIELD OF THE INVENTION

The invention relates to a system and method, using an automated blood cell separator, to prepare a high-quality hemoglobin solution as the raw material for manufacture of hemoglobin-based therapeutic oxygen carriers ("blood substitutes").

BACKGROUND OF THE INVENTION

The transfusion of stored human blood is an ancient standby of medical practice. However, its efficacy has never been rigorously shown, and the procedure has significant deficiencies. For example, even in the best medical centers, when the need for a transfusion is identified, treatment is delayed by the need to type and cross-match the patient's blood, then deliver the blood to the patient's bedside or to the operating or emergency room. In addition, some evidence suggests that blood transfusions may be immunosuppressive and that autologous donor lymphocytes may establish chimeras in the recipient. The risk of transmission of viral diseases by blood transfusion is well-recognized.

In spite of these problems, there is a growing worldwide need for transfusions as medical practice becomes more complex and the population ages. If the rate of transfusion in the United States is extended to the world population of 6 billion, a total annual demand for about 300 million units of red blood cells can be projected. No firm estimate of the number of units actually transfused is available, but the number could be as low as 90 million. Assuming the estimate is accurate, there is a potential shortfall of more than 200 million units per year worldwide. It is not likely that developing countries will be able to support the sophisticated blood banking procedures available in the developed world, nor will most of the developing countries be able to generate sufficient donor blood to meet demands because of the generally poor state of public health.

In an effort to address the potential shortfall in blood supply, therapeutic oxygen carriers, i.e., "blood substitutes", have been under intense development by both commercial and academic laboratories since the mid-1980's, and even longer in research laboratories. Significant problems have been overcome, including purification of hemoglobin to be used as a raw material, characterization of the solutions, and hemoglobin modification chemistry.

Whether or not a blood substitute succeeds in the marketplace depends on several key factors. First, it must be effective. However, a clear-cut test for efficacy has not been established. One possible test would be whether the product can effectively reduce exposure of patients to allogenic blood. Second, the product must be safe. Safety issues that have arisen to date center around the known property of hemoglobin to be vasoconstrictive. At least part of this property is the very strong binding of nitric oxide (NO) to hemoglobin as a heme ligand and at sulfhydryl sites. Third, a red cell substitute must successfully compete with blood for clinical use. Blood substitute products currently under development have plasma retention times ranging from 12 to 58 hours (half-time). Thus, they will either be used only in temporary situations or in settings where repeated doses can be administered.

Human blood has become extremely safe in the wake of intense scrutiny of the blood bank industry following the discovery that HIV can be transmitted by transfusion of blood products. In order to become a viable product, red cell substitutes must be safe and relatively inexpensive. A cost higher than that of blood will be supported only if there is a clear advantage in safety, efficacy, ease of use, or patient acceptance. Thus, as these blood substitutes near clinical use, the source, cost and supply of raw materials become more important. For products in clinical trials, raw hemoglobin is obtained either from outdated human banked blood, cows, or recombinant (*E. coli*) sources. Estimates are that one percent or less of stored blood becomes outdated, making only about 120,000 units of blood available for the manufacture of blood substitutes annually. Thus, the competition and cost for this outdated blood is high. Cow blood has the advantage that it can be obtained in large quantities. However, maintaining cows for this purpose requires strict health standards and veterinary care for the animals, frequent testing, and large amounts of land and food to support them. Furthermore, cow blood must be collected using special apparatus designed for that purpose. A recombinant source would be an ideal solution because of the reduced risk of contamination with human pathogens. However, recombinant hemoglobin requires extensive purification to separate the protein from other components of the fermentation, large volumes of water are utilized, and significant problems are encountered in handling the waste products. Such processing requirements result in a blood substitute product made with recombinant hemoglobin costing several times more than the cost of conventionally-banked blood.

The current procedures for preparing hemoglobin solution from human blood involve extensive process of washing pooled red cells with saline, sedimentation or diafiltration, gentle lysis with hypotonic buffers, and rigorous removal of red cell membranes. These procedures require large sterile containers and expensive filters, and take significant lengths of time to complete. Many of the components and solutions used in the process must be housed in cold and/or clean rooms. One reported pilot processing plant with a capacity of 5 liters of stroma-free red blood cell solution per week required four separate but connected rooms covering about 1000 square feet of laboratory space. The cost of production was about $1000/liter. (See Winslow and Chapman, "Pilot-scale preparation of hemoglobin solutions", *Meth. Enzymol.*, 231:3–16, 1994, the disclosure of which is incorporated herein by reference.) In addition to the significant disadvantage of the high cost of production, the large scale and complexity of this pilot set-up required several support personnel and created numerous opportunities for contamination.

In order to make blood substitutes available in the quantities needed to adequately address the projected deficit in worldwide blood supply, the existing methods for processing the raw materials needed to prepare the blood substitutes must be improved. The need remains for a method for preparing stroma-free hemoglobin for use in production of blood substitutes with reduced cost, complexity and risk of contamination of the product.

SUMMARY OF THE INVENTION

It is an advantage of the present invention to provide a method for preparation of stroma-free hemoglobin in a self-contained, automated apparatus.

It is another advantage of the present invention to provide a method to prepare a high-quality hemoglobin solution as the raw material for manufacture of blood substitutes using blood obtained at the point of collection, directly from donors, thus eliminating the need for typing and storage of blood, and reducing the risk of contamination.

In an exemplary embodiment, the method employs a commercially-available blood cell separator comprising a computer-controlled centrifuge having a rotor into which a blood processing bag containing donor blood is placed. Once the blood so is collected, the process is performed entirely within the enclosed centrifuge bowl, preferably in situ at the donor collection site. The centrifuge rotor includes one or a more processing chambers for receiving the processing bag(s). In the first step, the blood is centrifuged to separate the plasma from the cellular components. Supernatant, i.e., leukocytes, platelets, and plasma, is removed by using hydraulic fluid force through a flexible diaphragm in the blood processing bag and solenoid-controlled pinch valves, leaving the packed cells. The pinch valves function by pinching the tubing containing the solution, avoiding direct contact to keep the fluid path sterile. A rotating seal allows passage of fluids into and out of the blood processing bag while the centrifuge is rotating. After isolation of the red blood cells from other blood components, the red cells are washed with normal saline or other solution. The wash solution is removed by hydraulic force and transferred through tubing into a supernatant collection container. A photosensor is positioned to monitor the tubing leading to the supernatant collection container to detect the presence of red blood cells. If the red blood cells are detected, a stop or hold function is initiated by the system controller. The red blood cells are then lysed by hypotonic shock and centrifugal force is used to separate the red cell membranes (stroma) from the lysate, which is collected into a sterile container, leaving only the stroma in the centrifuge bowl. The final product can be used as raw material for any of the hemoglobin-based oxygen carriers currently being developed as red cell substitutes. All of these steps are performed within the bowl of the cell separator or saver to maintain sterility.

The ability to process the blood at the donation site provides for more rapid and less costly collection of red blood cells for making blood substitutes. Specifically, this procedure eliminates the need to type and store the units of collected blood, and units collected for this purpose could be pooled to reduce the cost of testing for infectious agents such as HIV or Hepatitis C.

BRIEF DESCRIPTION OF THE DRAWINGS

Understanding of the present invention will be facilitated by consideration of the following detailed description of preferred embodiments of the present invention taken in conjunction with the accompanying drawings, in which like numerals refer to like parts, and in which.

DETAILED DESCRIPTION OF THE PREFERRED EMBODIMENTS

Figure 1:
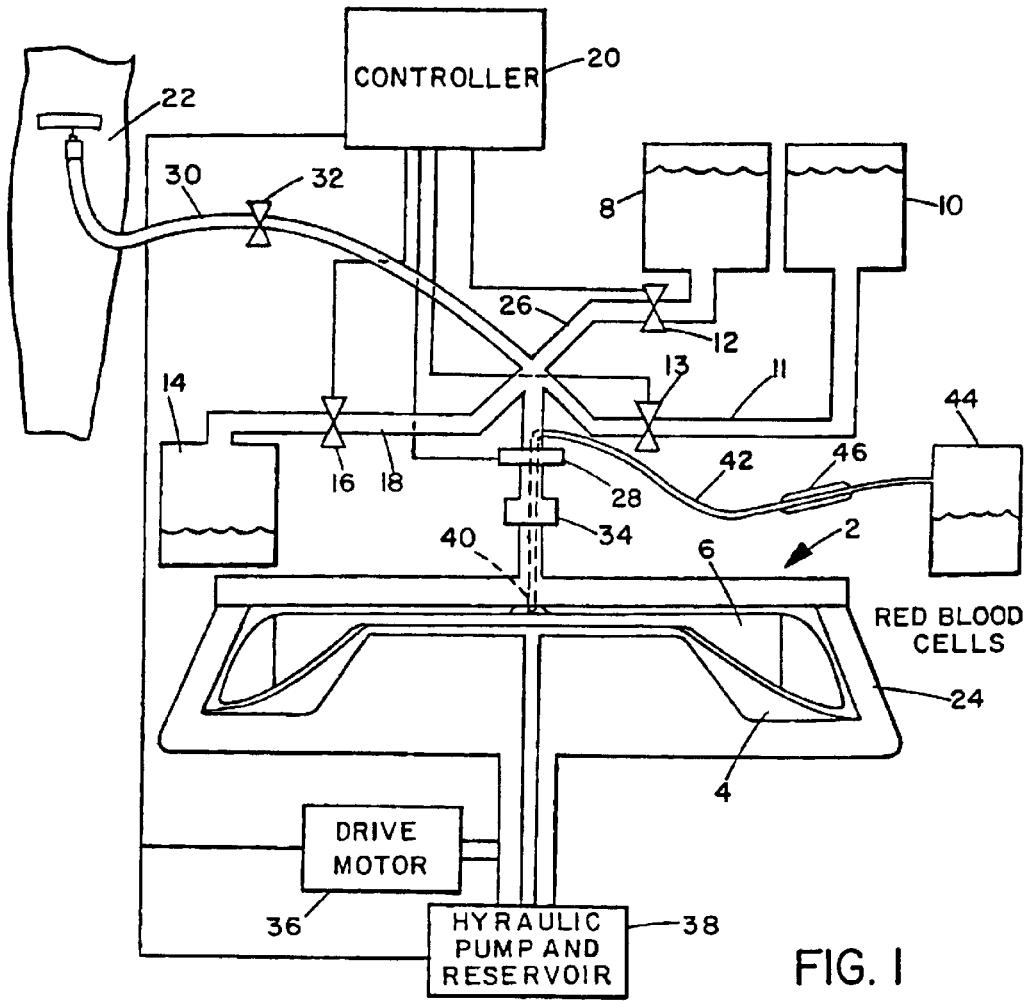
FIG. 1 is a diagrammatic view of red blood cell processor for use in preparation of stroma-free hemoglobin.

The method for production of stroma-free hemoglobin ("SFH") uses a conventional commercial blood cell processing apparatus which is diagrammatically illustrated in FIG. 1. Such systems are used for processing of separation of whole blood from a patient or donor into components. The red blood cells are collected, and the remaining components can be returned to the donor or discarded. The apparatus comprises a centrifuge 2 for retaining a blood bag 6, a plurality of reservoirs 8 and 10 containing processing solutions, a reservoir for receiving supernatant 14, a plurality of valves and a sterile tube harness connecting the various reservoirs to the blood bag 6, and a controller 20 for controlling the centrifuge and the valves. A disposable rotating seal 34 is included within the tube harness to allow passage of fluids into and out of the blood processing bag while the centrifuge rotor is rotating. The seal prevents fluids from leaking out of the fluid path and air from leaking into the fluid. Blood is collected from the donor (arm 22 is shown) through tube 30 and valve 32 directly into the blood bag 6, preferably for immediate processing. In the preferred embodiment blood bag 6 and the tube harness are parts of a pre-sterilized, disposable processing set. The valves function by pinching the tube so that there is no direct contact with the fluid in the tubes.

Centrifuge rotor 24 is activated to separate the red blood cells from the plasma. The centrifugal force provides the pumping for expression of the plasma to supernatant reservoir 14 (or back to the patient or donor, if desired). Specifically, a displacement chamber is included in the centrifuge rotor 24 comprising a hydraulically-operated diaphragm 4. The flow of a hydraulic fluid to and from the region under flexible diaphragm 4 is controlled by system controller 20 by controlling rotation of the centrifuge drive 36 and direction of a reversible hydraulic pump 38. Controller 20 causes valve 16 to open to permit the plasma to exit the blood bag through tube 18, then closes valve 16 after the plasma is removed. Complete removal of the plasma can be determined by use of optical detector 28, which detects the presence of red blood cells in the clear tubing. Saline solution from reservoir 8 is released through tube 26 into blood bag 6 by opening valve 12. Alternatively, an anti-bacterial agent, detergent or other appropriate cleansing solution can be used as the wash solution, or in addition to the saline solution, to remove any bacterial contaminants that might be in the blood. The centrifuge rotor rotates at a relatively low speed to provide agitation to wash the red blood cells. After washing, the rotational speed increases and controller 20 opens valve 16 allowing the centrifugal force and flexible diaphragm to express the wash solution into supernatant reservoir 14.

Once the wash solution is removed from blood bag 6, the red blood cells are lysed to separate the stroma from the hemoglobin by introducing distilled water to induce hypotonic shock. Distilled water, which is stored in reservoir 10 is transferred through tube 11 by opening valve 13. When red cells first come into contact with the distilled water, some of them lyse, liberating hemoglobin into solution. The cell-free component can be harvested at this time, and the distilled water infusion continues, liberating more and more hemoglobin as the ionic strength of the suspending medium decreases. With the centrifuge rotor rotating at a low speed to minimize damage to the hemoglobin, the stroma-free hemoglobin will be distributed throughout the bowl, while the red blood cells and membranes will become packed at the outer edge of the bowl. Since large amounts of distilled water may be required, several iterations will be required to liberate most of the hemoglobin. Removal of the hemoglobin is achieved via a sterilized port 40 in blood bag 6 through tube 42 into a sterile container 44. It may be desirable to include a filter 46 in the transfer pathway (tube) to remove the last traces of membrane particles. Given enough water and time, all of the hemoglobin should be removed, however, it may be necessary later to concentrate the hemoglobin solution, depending on the use for which it is intended. Determination of the completeness of hemoglobin extraction can be made by measurement of ion concentration in the hemoglobin solution. By connecting the conductivity meter to system controller 20, when the ionic concentration drops below a predetermined level, the process can be terminated. Selection of the predetermined level is based upon a balancing of the time versus efficiency of hemoglobin extraction, i.e., a cost-benefit analysis.

Other methods for inducing hypotonic shock for lysing the red blood cells are known and may be substituted for, or used in combination with, the distilled water rinse. Alternate lysing methods are described below in more detail.

The sterile container into which the hemoglobin solution is transferred can contain pre-measured reagents for preparation of blood substitute, including, for example, buffer salts, Traut's reagents and activated polyethylene glycol (PEG). Exemplary methods for preparation of the blood substitute are detailed in U.S. Pat. No. 5,814,601 and U.S. Pat. No. 5,296,465, the disclosures of which are incorporated herein by reference.

The method of processing takes place entirely within a disposable, pre-sterilized processing set, which preferably includes all tubing, reservoirs, centrifuge bowl and in-line filters. This closed system eliminates the risk of contamination.

The following examples are provided as illustrations only and are not intended to limit the scope of the invention.

EXAMPLE 1

An experimental apparatus for production of stroma-free hemoglobin from blood was constructed comprising a manifold for emptying bags of outdated blood; cross-flow filtration devices for washing, lysis and purification; a bioreactor for cross-linking hemoglobin; a preparative-scale HPLC apparatus; and a hood for final filling of product into sterile bags. The flow loops, including PFW distribution loops, were closed. All connections were of the sanitary triclamp type and were made in a laminar flow environment. The entire process required approximately 1000 ft$^2$ of laboratory space, exclusive of offices. This capacity of this pilot plant was about 5 liters per week and the cost of production was about $1000/liter.

The cross-flow filtration system consisted of three pumps, four tanks and four distinct filter packages. All construction materials were made from 316L stainless steel with internal finishes of 180 grit. Tubing was flexible and made of reinforced silicone. The hollow fiber filtration cartridges were nonhemolytic, nopyrogenic polysulfone membranes.

All solutions were chilled after preparation in jacketed stainless-steel 500-liter tanks. The red cell wash and lysis tank was glycol-jacketed for temperature control. The 500- and 10-kDa ultrafiltration loops used double-tube heat exchangers. The PFW was chilled prior to diafiltration of the concentrated hemoglobin. Rotary lobe pumps assured low shear conditions. Pressure profiles were monitored throughout the system and controlled to less than 20 psi. The pH of all solutions was maintained in the physiological range.

Sterility was maintained throughout the process. The cross-flow filtration system was housed in a class 100 environment. All process tanks, piping, and filters were either steamed in place with pure steam or sanitized chemically with 0.1 N NaOH. Sanitizing solutions were rinsed from the system with PFW. The sterility of the system was verified prior to processing and throughout the process by sampling for pyrogen using the Limulus amebocyte lysate (LAL) test.

Figure 2:
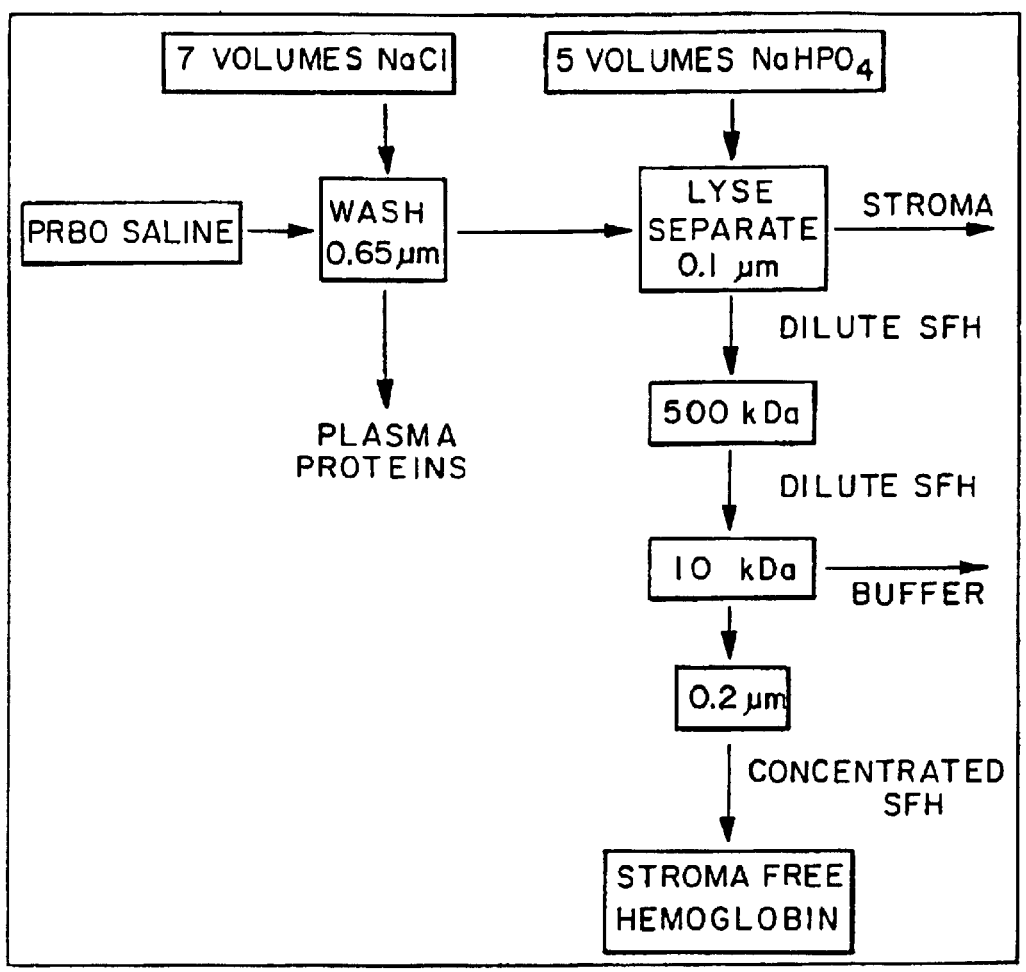
FIG. 2 is a flow diagram for production of stroma-free hemoglobin from packed red blood cells.

A flow diagram for a typical run for the production of SFH is shown in FIG. 2. Outdated human packed red blood cells (PRBC's) were used up to 4 weeks after outdate. All units were tested negative for HIV and hepatitis B antigens. In a typical batch, about 20 liters of PRBC's were pooled using a blood collection set with 80 liters of normal saline in a 100liter jacketed stainless-steel tank. The RBC's were washed with 7 volumes of chilled normal saline by diafiltration at a constant volume (80 liters) through three 0.65 $\mu$m hollow fiber membrane cartridges (total surface area 69 ft$^2$). To verify that plasma was removed, the filtrate was assayed for albumin as a marker for plasma proteins. During a typical wash, albumin concentration consistently decreased from more than 2 mg/ml to undetectable levels (<2 $\mu$g/ml). The RBC's were lysed slowly, and the stromata were removed by diafiltration with 5 volumes of chilled 10 mM NaHPO$_4$, pH 7.6, at a constant volume (80 liters) through 0.1 $\mu$m hollow fiber membrane cartridges. The filtrate of the 0.1 $\mu$m cartridge was directed to a 100-liter stainless-steel tank. It was then diafiltered at a constant volume (80 liters) through a 500-kDa membrane cartridge to remove any stroma particles. The filtrate (SFH) from the 500-kDa cartridges was then concentrated to 10 g/dl by circulation through three 10kDa hollow fiber membrane cartridges.

The resulting SFH solution was diafiltered with 6 volumes of Ringer's acetate, pH 7.4, and then transferred from the stainless-steel concentration tank through a 0.2 $\mu$m, 10-inch filter to a 40 liter stainless-steel holding tank. Finally, the SFH product was transferred under sterile conditions into plastic bags and frozen at −80° C. Alternatively, the SFH was transferred to a 70liter bioreactor for cross-linking.

Stroma-free hemoglobin solutions produced using the above apparatus and procedure were formulated either in water or in phosphate buffer. Methemoglobin concentration was routinely less than 1%, and the solutions could be stored indefinitely at −80° C. The rabbit pyrogen test was negative and the solutions were not contaminated by bacteria. Purity was assessed by HPLC analysis, and showed the solutions to be essentially free of non-hemoglobin proteins. Other quality control tests included oxygen binding (P50, Hill's parameter, n), pH, endotoxin (LAL test), and SDS gel electrophoresis. The results of these tests in a representative batch of SFH as produced are shown in Table 1.

TABLE 1

| Exemplary characteristics of SFH solutions | |
|---|---|
| Hemoglobin (g/dl) | 7.5 |
| Methemoglobin (%) | <1 |
| P50 (Torr, pH 7.4, 37° C.) | 12.0 |
| n (Hill's parameter) | 3.0 |
| P$_i$ ($\mu$m) | 42 |
| pH | 7.45 |
| Sterility | Pass |
| Pyrogen | negative |
| Endotoxin (EU/ml) | 0.02–0.10 |
| Free iron ($\mu g/\mu \lambda$) | 2.8 |

Perhaps the greatest concern in producing stroma-free hemoglobin, besides contamination, is the rigorous removal of membrane phospholipid components. Phospholipid is extremely difficult to measure, on a routine basis, so the simpler total phosphate assay was used. Although quite sensitive, it does not discriminate the source of the phosphate. Intracellular enzymes constitute a second group of red cell contaminants, and it is not clear whether removal of all red cell enzymes from the final product is even desirable, in view of their antioxidant activities.

"Units" of SFH collected in this way can be stored frozen indefinitely, and shipped either to a central processing facility (much as plasma processing is carried out in some locations) or pooled locally for quality control testing. Another advantage of the proposed system is that it can drastically reduce costs. At the present time, all collected blood is subjected to expensive viral testing, which is the largest single cost of blood collection. Using the new system, units can be pooled before testing, which greatly reduces the overall cost. Haemonetics estimates that the cost of collection of a unit of blood is $18, of which $15 is for viral testing. This cost could be reduced by a factor of 10 for tests done on 10-unit pools, for example.

Blood collected in this way may be acceptable for remanufacture into a "blood substitute", such as that disclosed in U.S. Pat. No. 5,814,601. However, it may not meet current FDA standards for donor blood. For example, patients with hemachromatosis are currently prevented by the FDA from donating blood for transfusion. This has prompted these patients to seek private physicians to carry out phlebotomies, at considerable cost to the patient. The Iron Overload Disease Society estimates that there may be as many as 1.5 million individuals in the U.S. alone with significant iron overload. The society has records of approximately 5,000 patients who are in regular phlebotomy programs, which remove about 6 units/year, or 30,000 units. The red cell substitute has established a dose-equivalence such that 1 g/dl of plasma hemoglobin is as effective in a hemorrhage model as 7 g/dl of red cell hemoglobin. Thus, this group of patients alone could supply the raw materials for as many as 150,000 units of artificial blood per year.

EXAMPLE 2

In an embodiment of the invention, a self-contained, portable unit designed to collect donor/patient blood at the bedside is used. Appropriate systems for this application include the Haemonetics MCS+8150 Blood Collection System in (Haemonetics Corporation, Braintree, Mass.) and the COBE 2991 Cell Processor (COBE Laboratories, Inc., Lakewood, Colo.). Blood is collected in a CP2D/AS-3 anticoagulant/additive system, at 1:16 ratio of anticoagulant to anticoagulated blood. The machine is configured to collect either one or two units of red blood cells from a single donor in approximately 25 minutes. Each unit collected yields approximately 180 ml of packed red blood cells ("RBC") and 400 ml of plasma. The following relationships can be used to determine efficacy of the separation:

post-process RBC countx post-process weight/×100=% RBC recovery pre-process RBC countx preprocess weight The number of leukocytes remaining within the packed red blood cells should be less than $5\times10^8$. The absolute white blood cell ("WBC") count is:

WBC count converted to milliliters×product volume in milliliters, while the percent remaining is:

post-process WBC countx post-process weight×100=% WBC remaining pre-process WBC countx pre-process weight Examples of a basic commercial blood cell processing system are provided in U.S. Pat. No. 4,303,193 of Latham, Jr., and U.S. Pat. No. 5,921,950 of Toavs, et al. The disclosures of these patents are incorporated herein by reference. Generally, commercial blood cell processing systems use a self-balancing centrifuge for separating blood from a human donor into two components, one rich in plasma, the other rich in cellular components. This apparatus is intended to be used immediately adjacent the blood donor/patient. The pathway for the flow of the blood is completely disposable processing set including a phlebotomy needle and blood-compatible tubing connecting the phlebotomy needle to a flexible blood processing bag having a capacity of about 630 ml. Also included in this processing set are a tube harness, a rotating seal and a supernatant collection container. The rotating seal allows passage of fluids into and out of the blood processing bag while the centrifuge rotor is rotating. The seal prevents fluids from leaking out of the fluid path and air from leaking into the fluid. The tube harness provides a sterile fluid path for introduction of wash solutions to the red cells. Three valves control the flow of blood or wash solutions into the blood processing bag. Each valve is a solenoid-controlled pinch valve, under the control of the system computer, and have no direct contact with the fluid in the tubing. A sterile outlet port at the outer edge of the processing bag enables transfusion of the processed cells directly from the bag into a sterile container.

The bag is configured to be supported within a contoured processing chamber in the centrifuge rotor so that the second blood component travels along a short internal bag dimension to achieve separation. A displacement chamber having a hydraulically-operated diaphragm is also positioned within the blood processing chamber of the centrifuge rotor. The flow of hydraulic fluid to and from the region under the flexible diaphragm is controlled by rotation of the centrifuge drive and pinch valve solenoids. The hydraulic system consists of a positive displacement piston-type pump assembly, flow rate controls and switches, along with the fluid flow network of piping and reservoir (plastic bag.) The pump is driven by a variable-speed reversible motor. The volume capacity of the pump is adjusted for approximately 600 ml. Pump motor control is driven forward at a set rate to express the supernatant by exerting pressure on the blood processing bag, forcing the supernatant fluid out of the bag through one of the open valves to the supernatant collection container. This continues until red cells are sensed through a photosensor, the supernatant-out volume is reached, or a stop or hold function is initiated. The pump is driven in the reverse direction to draw fluid from the centrifuge hydraulic fluid chamber and from the reservoir. The centrifuge rotor can then be stopped to allow return of second blood component to the donor. Because all of the functions are under computer control, there is minimal intervention by the operator and, thus, little opportunity for operator error.

The volume of the centrifuge bowl is approximately 250 ml, and the centrifuge speed is approximately 4,000 rpm. Blood entering the centrifugal field is diluted with sterile saline, and red cells are concentrated by continuous removal of non-red cell components and plasma. The goal is to reduce the amount of serum albumin to as low a level as possible, preferably to become undetectable. The non-red blood cell components can be discarded or used for other purposes.

Evaluation of serum protein removal after the RBC wash step is conducted using procedures prescribed by the manufacturer of the blood cell processor. For example, in the COBE 2991 Cell Processor, after the red blood cells are washed, a 1 ml sample is extracted through the sterile port in the blood bag, is centrifuged in a laboratory centrifuge, and the supernatant is collected. A commercially-available protein chemistry dipstick wet pad can be used to test the supernatant, with the color change being indicative of protein level. Protein level should be trace (15–30 mg/dl) or less, representing a plasma reduction of greater than or equal to 96%.

Figure 3:
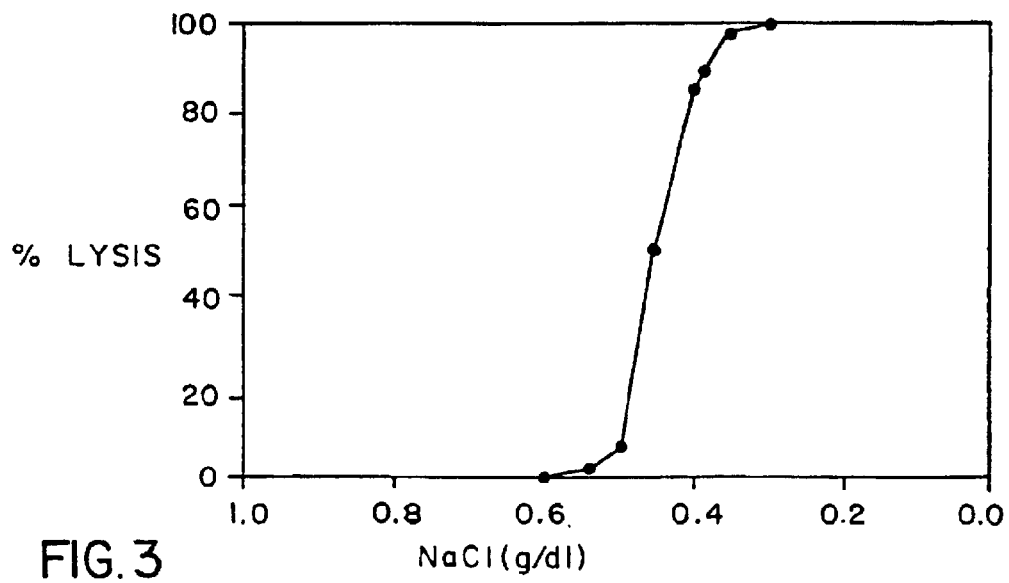
FIG. 3 is a block diagram of the process flow according to the present invention.

After the initial washing period, the saline is replaced by distilled water. Referring to FIG. 3, it can be seen that when red cells first come into contact with the distilled water, some of them lyse, liberating hemoglobin into solution. Conditions for lysis are discussed below. The cell-free component can be harvested at this time, and the distilled water infusion continues, liberating more and more hemoglobin as the ionic strength of the suspending medium decreases. Given sufficient time, it is possible to remove all of the hemoglobin, leaving only red blood cell ghosts in the centrifuge bowl.

The volume of the hemolysate depends on the amount of distilled water needed to achieve a desired level of lysis. However, the hemoglobin solution may need to be concentrated further, depending on the use for which it is intended. Because NaCl may accompany the hemoglobin solution, subsequent purification may be required. A rapid, sensitive measure of the ionic strength of the final solution can be obtained by conductivity measurement.

Conditions for Lysis of Human Red Blood Cells

In spite of its long lifetime within circulating red cells, hemoglobin is a fragile protein. It is made up of 4 polypeptide subunits, 2 $\alpha$ and 2 $\beta$. An $\alpha$ and a $\beta$ chain are tightly linked into an $\alpha\beta$ subunit, and 2$\alpha\beta$ subunits form a less stable tetramer, the fully formed hemoglobin molecule. Each of the 4 subunits contains an iron-prosthetic group, heme. The iron atom is maintained in the reduced, $Fe^{++}$ state in order to bind oxygen. Maintenance of this reduced state is by the presence of a number of enzyme systems within the red blood cell. When hemoglobin is liberated from the cell, this protection is no longer present, and a series of events occur which ultimately leads to degradation of the molecule. These events are oxidation of iron, loosening of the hermoglobin linkage, release of heme, separation of tetramers to dimers, denaturation of globin, and, eventually, precipitation. In the production of a red cell substitute, it is therefore extremely important to handle the protein very gently in order to prevent one or more of these degradation steps. Failure to do so will lead to loss of raw material, and formation of precipitates which must be filtered out. Furthermore, even partially denatured or degraded hemoglobin molecules do not bind oxygen reversibly and therefore are useless as oxygen carriers.

In general, there are three methods to lyse human red cells. First, they can be frozen and thawed repeatedly. The formation of ice within and around the cells disrupts the membranes and hemoglobin is liberated. However, lysis using this method is notoriously incomplete, and the hemoglobin denaturation can occur. In the second method, organic solvents, such as $CCl_4$ or toluene can be used. This method is more efficient, however, the solvents can also adversely affect the stability of the protein.

A third method is osmotic lysis, such as described above. The susceptibility of red cells to osmotic lysis is well known.

Estimated Process Efficiency

Yield according to the protocol for the COBE 2991 Cell Processor are reported as a mean RBC recovery of 82%, with removal of up to 99% of plasma and 93.4% of white blood cells. Using the inventive method to centrifugally wash and lyse red blood cells gives approximately 40 g of stroma-free hemoglobin ("SFH") from a starting mass of 50 g, providing an estimated yield of 80%. Thus, a final yield is estimated to be approximately 66% mass from starting material to processed SFH.

A problem in hemoglobin production is protein denaturation. Hemoglobin is sensitive to the effects of dilution, pressure, shear, temperature and pH changes. these factors can lead to problems involving oxidation, precipitation, heme loss, and subunit dissociation. Thus, it is important that all process steps be performed at uniform and low temperature. For example, the COBE 2991 Cell Processor can be refrigerated to maintain a temperature of 4° C. Furthermore, agitation should not be too vigorous, pH changes should not be abrupt, and pressures should not reach high levels.

Characterization and Quality Control

Measurement of stromal contamination can be performed by using the total phosphate assay. Extraction of phospholipid from a hemoglobin solution can be difficult, so the total phosphate assay is an easier and less costly procedure. Although quite sensitive, this assay cannot discriminate the source of the phosphate.

Intracellular enzymes constitute a second potential group of red blood cell contaminants, however, it is possible that some contamination of this type may be acceptable in blood substitutes. Analytical FPLC can be used to evaluate the homogeneity of stroma-free hemoglobin product using a 280 nm filter to resolve SFH from non-hemoglobin proteins.

Endotoxin measurement can be performed using a kinetic turbidimetric assay based on the initiation of the Limulus amebocyte lysate (LAL) coagulation cascade. Such assays are well known in the art. (See, e.g., Cohen, et al., *Biomedical Applications of the Horseshoe Crab (Limulidae)*, 1979, Alan R. Liss, Inc., New York.)

Stroma-free hemoglobin solution pH and conductivity can be measured using conventional pH and conductivity meters, such as those in the Accumet line from Fisher Scientific Co., Pittsburgh, Pa. Spectral analysis can provide estimates of hemoglobin concentration and the amount of methemoglobin in the solutions. Such analysis can be performed using a rapid scanning diode array spectrophotometer, such as the Milton Roy 3000, in the Soret and visible regions, with evaluation performed according to the multicomponent analysis technique described by Vandegriff and Shrager ("Evaluation of oxygen equilibrium binding to hemoglobin by rapid scanning spectrophotometry and singular value decomposition", *Meth. Enzymol.* 232:460–485, 1994), which is incorporated herein by reference.

The most sensitive test to determine the functional state of a hemoglobin solution is to measure its oxygen binding curve. One such method entails the linear consumption of oxygen in a closed optical cuvette by a novel enzyme system. As the oxygen is depleted, repeated visible spectra are taken, while $PO_2$ is measured simultaneously with a Clark-type electrode. The hemoglobin is diluted in 0.1 M bis-Tris propane or phosphate buffer to a concentration of approximately 60 $\mu$m (in heme). The reaction takes approximately 15 minutes. The reaction uses protocatechuic acid (PCA, Sigma Chemical Co., St. Louis) as substrate and consumes one mole of $O_2$ for each mole of PCA converted to product by the enzyme protocatechuic acid 3,4- dioxygenase (PCD, Sigma Chemical Co., St. Louis). After the experiment, $PO_2$ values are matched to spectra. The spectra are subjected to multi-component analysis and curve-fitting procedures to determine the parameters of the oxygen binding curve (P50, Hill's parameter, n). In the course of analyzing these spectra, the relative proportion of methemoglobin is calculated for each step in the deoxygenation. Furthermore, the method and analysis reveals the presence of any additional hemoglobin components, such as products of denaturation and degradation.

The hemoglobin solutions produced using this invention are also characterized by isoelectric focusing (IEF) on agarose and polyacrylamide in the pH ranges 8.5 to 5.5. The subunit structure is evaluated by sodium dodecyl sulfate-polyacrylamide gel electrophoresis. Spectral analysis provides estimates of the hemoglobin concentration and the amount of methemoglobin and carboxyhemnoglobin in the solutions. Spectra are collected on a rapid scanning diode array spectrophoitometer in the Soret and visible regions. Spectra are evaluated by multicomponent analysis. Other quality control measures include measurement of hemoglobin concentration, pH and conductivity. Additional quality control measures are instituted, as needed.

EXAMPLE 3

Preparation of Modified Hemoglobin Using the Described Invention

Figure 4:
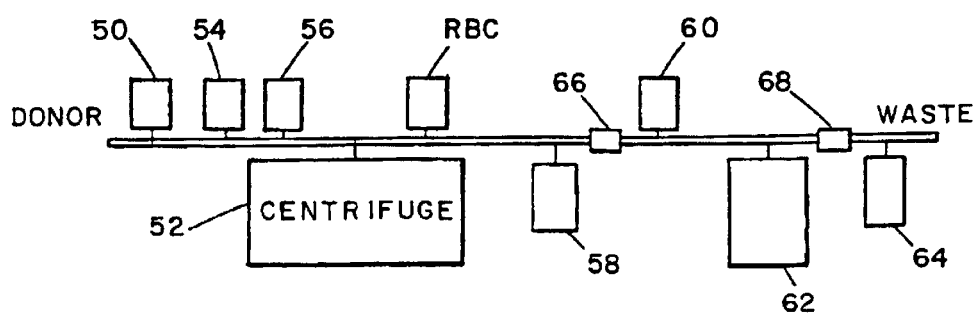
FIG. 4 shows a schematic diagram of one possible configuration of the invention to produce a "blood substitute".

The present invention can further be used to prepare a modified hemoglobin solution ("the product") using the stroma-free hemoglobin (SFH) solution prepared in the described modified cell separator device as shown in FIG. 4.

The red blood cells can be obtained from any source, including animal or human, stored or fresh, or even outdated human units obtained from a blood bank. The modification procedure can also use a hemoglobin solution prepared by any means, including the present invention, or by other methods, including recombinant hemoglobins. If donor blood is used, it is first mixed with an anticoagulant 50, washed in the centrifuge bowl 52 with normal saline 54 and lysed with distilled water 56. Plasma, platelets and white blood cells fractions are removed and stored in a separate container 58. The hemoglobin solution (SFH) 60 is placed either into a separate reservoir 62, or into the centrifuge bowl 52, where chemical modification is carried out. After filtration, the final product is collected in a sterile container 64 which can be stored for future use.

In cases where the SFH prepared in the described apparatus is to be processed further into a product, the SFH is collected into a reservoir which contains the premeasured reagents for the chemical modification. In the preferred method, the reagents are buffer salts, iminothiolane and activated polyethylene glycol. At the end of the reaction period, the modified hemoglobin (PEG-Hb) is collected into a plastic bag or other storage receptacle and stored.

Although reaction with PEG is the preferred hemoglobin modification, any described modification can be carried out by the described apparatus of the present invention, and these procedures are well known in the field of blood substitute preparation. Such modifications might include, as examples, internal cross-linkers, polymerization reactions, or surface modification of hemoglobin with dextrans, starches, or other synthetic or natural polymers.

The product can be further purified by passing it through filters 66 and 68 in FIG. 4). Such filters, and ultracentrifugation devices, for example, could be size exclusion filters, ion-exchange filters, mixed-bed ion exchangers, activated charcoal filters or other in-line filters used in protein purification or dialysis procedures. The product can be formulated with any solution of salts or other materials.

Sterilization of the product can be performed in the same apparatus by any number of procedures, including solvent-detergent treatment, gamma irradiation, nanofiltration, methylene blue or similar derivative, or any other means for inactivating or removing organisms such as bacteria and viruses.

The inventive method provides means for more rapid and less costly collection of red blood cells which are needed for producing blood substitutes that are capable of addressing the significant worldwide shortfall in available blood for transfusion. The inventive method can be used for processing of outdated blood, but is most advantageously used in situ at the donor/patient's bedside. Because the process is performed in a computer-controlled, fully self-contained apparatus, handling is minimized, and risk of contamination is eliminated. The procedure also eliminates the need to type and store units of collected blood, and units collected for this purpose could be pooled to reduce the cost of testing for infectious agents.

It will be evident that there are additional embodiments and applications which are not specifically included in the detailed description, but which fall within the scope and spirit of the invention. The specification is not intended to be limiting, and the scope of the invention is to limited only by the appended claims.

What is claimed is:

1. A method for isolating hemoglobin from a starting solution containing red blood cells, the method comprising the steps of:
    (a) separating the red blood cells from the starting solution;
    (b) washing the red blood cells in wash solution;
    (c) contacting the red blood cells with a hypotonic solution to produce stromata and a hemolysate containing hemoglobin having an ionic strength, wherein step (c) further comprises measuring the ionic strength of the hemolysate; and
    (d) separating the hemolysate from the stromata;
    wherein steps (c) and (d) are simultaneously or sequentially repeated until the ionic strength of the hemolysate is below a predetermined level.

2. The method of claim 1, wherein the wash solution further comprises a normal saline solution.

3. The method of claim 1, wherein the wash solution further comprises an agent for killing bacteria.

4. The method of claim 1, wherein the wash solution further comprises an agent to remove or inactivate organisms.

5. The method of claim 1, wherein steps (a) through (d) are performed within a single processing container.

6. A method performed within a cell processing apparatus for isolating hemoglobin from a solution containing red blood cells and plasma, the method comprising the steps of:
    (a) collecting the solution in a sterile processing set comprising a processing bag and a tube harness, wherein the processing bag is disposed within a centrifuge in the cell processing apparatus;
    (b) separating the red blood cells from the plasma by rotating the processing bag within the centrifuge;
    (c) expressing the plasma from the processing bag;
    (d) introducing a washing solution into the processing bag to wash the red blood cells;

(e) expressing the supernatant after washing;

(f) lysing the red blood cells to produce stromata and a hemolysate containing hemoglobin having an ionic strength, wherein said lysing step further comprises exposing the red blood cells to a hypotonic solution;

(g) separating the hemolysate from the stromata by rotating the processing bag in the centrifuge; and (h) removing the hemolysate through a sterile port in the processing bag.

7. The method of claim 6, wherein the steps of separating the hemolysate from the stromata further comprises the steps of:

removing the hemolysate produced when the hypotonic solution initially contacts the red blood cells; and continually removing additional hemolysate produced as the ionic strength of the hemolysate decreases.

8. The method of claim 7, further comprising the steps of:

measuring the ionic strength of the hemolysate;

adding additional hypotonic solution; and simultaneously carrying out or repeating the steps of adding additional hypotonic solution and removing hemolysate until the ionic strength is below a predetermined level.

9. A method for isolating hemoglobin from a solution containing red blood cells within a processing container in a cell processing apparatus, the method comprising the steps of:

(a) washing the red blood cells in the processing container with a saline solution;

(b) lysing the red blood cells in the processing container to produce stromata and a hemolysate containing hemoglobin having an ionic strength, wherein said lysing step further comprises measuring the ionic strength of the hemolysate formed by exposing the red blood cells to a hypotonic solution;

(c) separating the hemolysate from the stromata and red blood cells within the processing container; and (d) extracting the hemolysate from the processing container;

wherein the steps of lysing and separating are simultaneously carried out or sequentially repeated until the ionic strength of the hemolysate is below a predetermined level.

10. The method of claim 9, wherein the step of separating further comprises centrifuging the processing container within the apparatus to pack the stromata and red blood cells.

11. The method of claim 9, wherein the step of washing further comprises adding a detergent, antibacterial or antiviral agent to the saline solution.

12. A method for preparing a chemically modified hemoglobin solution from a starting solution containing red blood cells, the method comprising the steps of:

(a) separating the red blood cells from the starting solution;

(b) washing the red blood cells in wash solution;

(c) contacting the red blood cells with a hypotonic solution to produce stromata and a hemolysate containing hemoglobin having an ionic strength, wherein step (c) further comprises measuring the ionic strength of the hemolysate;

(d) separating the hemolysate from the stromata; and (e) mixing the hemolysate with a reagent adapted to chemically modify the hemoglobin to form a chemically modified hemoglobin solution;

wherein steps (c) and (d) are simultaneously or sequentially repeated until the ionic strength of the hemolysate low a predetermined level.

13. The method of claim 12, wherein the reagent comprises activated polyethylene glycol.

14. The method of claim 12, further comprising the step of filtering the chemically modified hemoglobin solution.

15. The method of claim 12, farther comprising the step of sterilizing the chemically modified hemoglobin solution.

* * * * *

UNITED STATES PATENT AND TRADEMARK OFFICE
CERTIFICATE OF CORRECTION

PATENT NO. : 6,773,613 B1
DATED : August 10, 2004
INVENTOR(S) : Robert M. Winslow et al.

It is certified that error appears in the above-identified patent and that said Letters Patent is hereby corrected as shown below:

Column 14,
Line 31, delete "low" and insert -- is below --
Line 36, delete "farther" and insert -- further --

Signed and Sealed this

Fourteenth Day of December, 2004

JON W. DUDAS
*Director of the United States Patent and Trademark Office*